United States Patent [19]

Riess et al.

[11] 4,178,686

[45] Dec. 18, 1979

[54] ARTIFICIAL TOOTH WITH IMPLANTABLE TOOTH ROOT

[75] Inventors: Guido Riess, Marienplatz 7, 8100 Garmisch-Partenkirchen, Fed. Rep. of Germany; Helmut Heide, Schwalbach, Fed. Rep. of Germany; Roland Reiner, Eschborn, Fed. Rep. of Germany; Kari Köster, Lorsbach, Fed. Rep. of Germany; Günther Brötz, Stierstadt, Fed. Rep. of Germany

[73] Assignee: Guido Reiss, Garmisch-Partenkirchen, Fed. Rep. of Germany

[21] Appl. No.: 867,336

[22] Filed: Jan. 6, 1978

[30] Foreign Application Priority Data

Jul. 23, 1977 [DE] Fed. Rep. of Germany ....... 2733394

[51] Int. Cl.² .......................................... A61C 13/00
[52] U.S. Cl. .................................................. 433/201
[58] Field of Search .................... 3/1.9, 1.91; 32/10 A; 128/92 G

[56] References Cited

U.S. PATENT DOCUMENTS

| 3,827,145 | 8/1974 | Richards | 32/10 A |
|---|---|---|---|
| 3,905,047 | 9/1975 | Long | 3/1.9 |
| 3,919,773 | 11/1975 | Freeman | 32/10 A |
| 3,955,280 | 5/1976 | Sneer | 32/10 A |
| 3,971,134 | 7/1976 | Bokros | 32/10 A |
| 4,051,598 | 10/1977 | Sneer | 32/10 A |
| 4,097,935 | 7/1978 | Jarcho | 32/10 A |

*Primary Examiner*—Robert Peshock
*Attorney, Agent, or Firm*—Scully, Scott, Murphy & Presser

[57] ABSTRACT

An artificial tooth with an implantable root adapted to permanently grow together with the jawbone and, also under high mechanical loads as is the case for natural teeth, will not allow for the production of a rejection or repelling reaction between the natural bone and the implant. The tooth root is essentially constituted of a biostable polymer matrix which is compatible with human tissue, in which there is introduced reabsorbable bioreactive calcium phospate in a finely dispersed form, which is encompassed by a thin porous layer of non-reabsorbable calcium phospate, and into which there is inserted a core as a connecting member for the mounting of a dental superstructure in the form of a tooth crown, a fastening element for dental bridges or the like. In the region of the tooth neck which is encompassed by the gingiva, an intermediate member is located between the tooth root and the superstructure, which is formed of tissue-compatible material and which supports the close contact of the gingiva, and by means of which the dental superstructure is connected with the tooth root in a shock-absorbent manner.

20 Claims, 3 Drawing Figures

ARTIFICIAL TOOTH WITH IMPLANTABLE TOOTH ROOT

BACKGROUND OF THE INVENTION

1. Field of the Invention

The present invention relates to an artificial tooth with an implantable tooth root.

2. Discussion of the Prior Art

The presently known and, at this time, mostly utilized implants have their anchoring portion constituted of metal and are in the configuration of a plate, needle or screw. It is common to all of these implantable bodies that the anchoring of the prosthesis on the bone is predicated on a purely mechanical interengagement or meshing with the bone. Hereby, a direct, transitionless growing together of the implant with the bone is not possible, but it is more likely that in the bordering region between the bone and the implantable body there is presently formed a more or less thick connective tissue-like encapsulation which, upon loading of the prosthesis, increases still further in size and thickness and then produces the beginning of a rejection reaction. This process, in accordance with present scientific knowledge, can be traced back to an interaction of biochemical and biomechanical factors.

Further known are artificial tooth roots which are constituted of a metallic core with a covering of pure $Al_2O_3$ oxide ceramic (bioinert materials). In order to increase the external surface thereof, these $Al_2O_3$ roots are provided with cuts, ribbing structure or bores into which the jawbone is intended to grow in order to thereby produce a mechanical intermeshing. However, it has been determined that prosthesis shanks which are formed of $Al_2O_3$ oxide ceramic, in particular under high mechanical loads in the bone/ceramic boundary region, are separated through a connective tissue capsule so as to inhibit the formation of a direct interconnection with the bone. During the course of a dynamic transformation process of the bone, this connective tissue membrane can increase in thickness at locations subjected to higher loads; thereby leading to loosening and finally the rejection or repelling of the prosthesis, respectively, the implant. Analogous objections are present against implants which are formed of other bioinert materials, among which there may be also calculated, for instance, implants formed of glass or silicon material.

In a further group of known dental prostheses, specialized glass ceramic materials are utilized as prosthesis shank which, based on their composition, are intended to exert a bioactive effect on the bone formation, by means of which it is hoped to achieve a direct growing together of the bone and of the implant. This glass ceramic and the enamel required to be adhered to metal contain materials foreign to the human body, so as to at least render questionable any long-term compatibility with the body tissue.

SUMMARY OF THE INVENTION

Accordingly, it is an object of the present invention to provide an implantable artificial tooth, in effect, a tooth with an implantable root, which can permanently grow together with the jawbone and, also under high mechanical loads as is the case for natural teeth, will not allow for the production of a rejection or repelling reaction between the natural bone and the implant.

The foregoing object is inventively achieved in that the tooth root is essentially constituted of a biostable polymer matrix which is compatible with human tissue, in which there is introduced reabsorbable bioreactive calcium phosphate in a finely dispersed form, which is encompassed by a thin porous layer of non-reabsorbable calcium phosphate, and into which there is inserted a core as a connecting member for the mounting of a dental superstructure in the form of a tooth crown, a fastening element for dental bridges or the like whereby, in the region of the tooth neck which is encompassed by the gingiva (gum skin), an intermediate member is located between the tooth root and the superstructure which is formed of tissue-compatible material and which supports the close contact of the gingiva (gum skin), and in which the dental superstructure is connected with the tooth root in a shock-absorbent manner.

The above-mentioned materials and the construction of the tooth root facilitate an actual growing together of the implant with the jawbone and thus produce a stable, load-resistant foundation for the dental superstructure which is mounted thereon in a specialized manner. The close edge contact or sealing in the region of the gingiva effects a complete protective screening of the implant support against the milieu or environment of the mouth. An excessive load acting on the implant support is finally prevented through the inventive, shock-absorbent mounting of the superstructure on the tooth root so that, by means of this measure, there is produced a flexibility for the superstructure, in essence dental prosthesis, which simulates the natural conditions in the tooth and which, during unfavorable loading relationships, will reduce and correct an unfavorable force effect acting on the anchoring in the jaw.

In a suitable embodiment of the invention, the reabsorbable bioreactive, sintered calcium phosphates are approximately uniformly embedded in the exterior region of the polymer matrix in the configuration of spherically-shaped particles having a diameter of between 0.2 and 1.5 mm, and these particles are encompassed by a thin porous layer of non-reabsorbable sintered calcium phosphate. Thus, the spherically-shaped particles which are embedded in the polymer matrix possess a multicomponent shell-like construction and, namely, wherein the nucleus inventively consists of a reabsorbable calcium phosphate ceramic in conformance with the composition of tricalciumphosphate ($3CaO.1P_2O_5$), and carries a thin shell of another non- or barely reabsorbable calcium phosphate ceramic, namely, formed from tetracalciumphosphate ($4CaO.1P_2O_5$).

This inventive construction affords a reduced reabsorption of the calcium phosphate components and a bioreactive relationship of the tooth root with regard to the bone. The tricalciumphosphate, in effect, the nucleus of the spherically-shaped particles, is reabsorbed relatively rapidly and simultaneously replaced by newly formed bone (compare K. Köster, E. Karbe, H. Kramer, H. Heide and R. König: Experimenteller Knochenersatz durch resorbierbare Calcium-phosphat-Keramik; Langenbeck's Archiv für Chirurgie 341, 77–86, (1976). The tetracalciumphosphate possesses a similar positive reaction with respect to the bone in view of the formation of a close bone-ceramic binding, but it is not reabsorbed. In this manner, during the root construction of the inventive artificial tooth there is produced an intimate binding or connective tissue with the bone in that newly formed bone tissue grows into the reabsorbed areas (areas of tricalciumphosphate) of the external root surface so that the new bone tissue pushes against the not reabsorbable tetracalciumphosphate ceramic forming the inner surfaces of the pores and thereby always the new bone contacts a bone-compatible material.

In order to facilitate the reduced reabsorption and the rapid growing in of newly formed bone into the implanted tooth root in contact with the jawbone, in a further advantageous embodiment of the invention, the approximately spherically-shaped calcium phosphate particles are found only in the outer surface region of the tooth root, and are cut along approximately one-fifth to one-half of their circumference, in such a manner, that only on the side which faces towards the polymer matrix there is present the coating of a non- or barely reabsorbable sintered tetracalciumphosphate in the form of the porous particle covering. The polymer matrix of the tooth root, for example, consists of polymethylmethacrylate and copolymers, of polypropylene or of polyethylene and suitably contains in a uniform distribution 10 to 20 percent by weight of tricalciumphosphate as a finely dispersed filler material, whereby also the remaining portions of the artificial root become compatible with the tissue and allow for the direct growing on thereto of the bone.

Basically, the tooth root can be produced in suitable configurations and sizes, also in a saddle form, in accordance with available implantation space. Thus, an extremely important advantage of the invention resides in that the artificial tooth root need not be constructed so as to imitate the natural tooth root, but can be imparted practically every suitable configuration which is correlated with the mechanical requirements or the conditions present during implanting. Inventively, the tooth root has thereby a differing form which corresponds to the available implantation space. Preferably the tooth root is constructed so as to be rotationally symmetrical, and in particular cylindrically or conically reducingly tapered towards its free end.

Since the artificial tooth root should conform to the implantation space in its external form and dimensions it is possible, in a simple manner, and with the aid of a bone milling cutter in a simple and saving procedure, upon occasion pursuant to a template, to work the implantation space into the jawbone.

In a further advantageous embodiment of the invention, the dental superstructure which is, for example, in the shape of a tooth crown, or a fastening element for dental bridges or the like, is seated on a metal sleeve which is filled with silicon rubber or a similar elastic material and into which there extends a bolt which is detachable, for instance, threadedly connected with the core of the tooth root. The force which is exerted on the superstructure is damped through intermediary of the silicon rubber on the bolt and conducted from the latter to the tooth root. This so-called "epimobile" fastening of the superstructure on the tooth root, and thereby the arrangement of the shock-absorbent mechanism within the superstructure, namely exteriorly of the actual implant, in contrast to a contemplatable corresponding arrangement in the tooth root, as has been acknowledged in actual practice, leads to an infective shock-absorbent effect with suitable leverage.

Inventively, the intermediate member is unitarily formed beneath the tooth root core of tissue-compatible metal, coated metal, metal ceramic or the like. Additionally, provided in the intermediate member is an inner bore for the bolt for effecting the fastening of the superstructure. In order to attain a good degree of growing on of the gingiva (gum skin) and a closely or sealingly encompassing tooth neck, in a further suitable embodiment of the invention the intermediate member is constructed in the form of a disclike member having a concavely curved annular edge.

BRIEF DESCRIPTION OF THE DRAWINGS

Reference may now be had to preferred exemplary embodiments of the invention hereinbelow described in detail, in conjunction with the accompanying drawings; in which.

DETAILED DESCRIPTION

Figure 1:
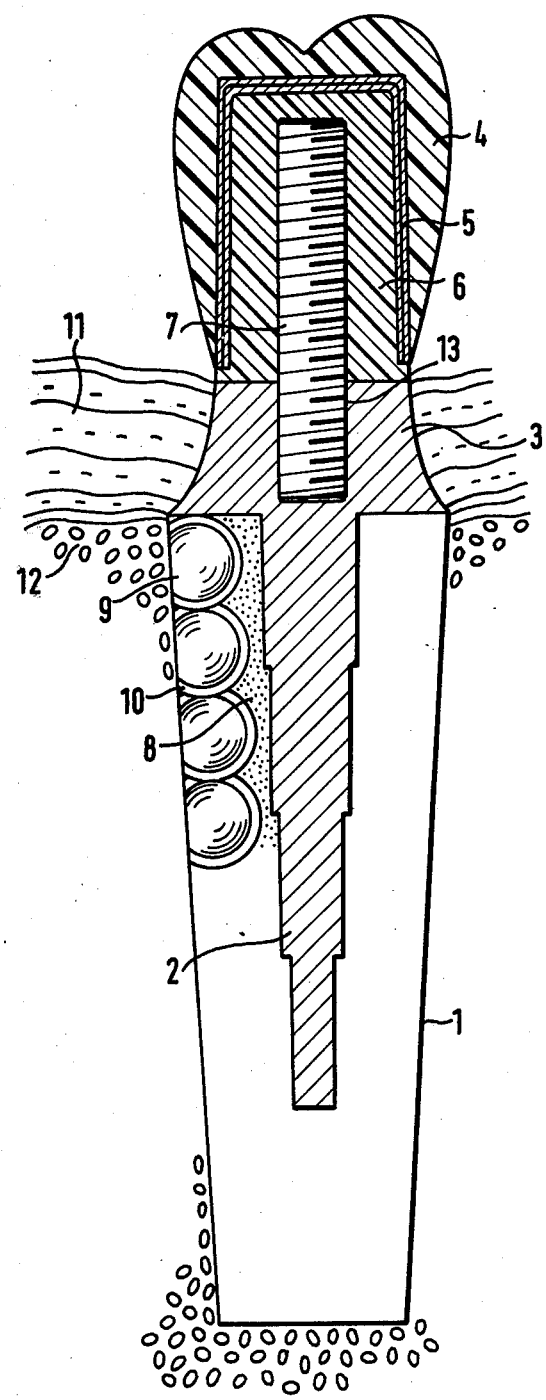
FIG. 1 is an enlarged illustration, in an axial section, of the principal construction of an embodiment of the artificial tooth pursuant to the present invention.

Referring now in detail to the drawings, in accordance with the illustration in FIG. 1 the inventive artificial tooth is essentially constituted of the enossal root 1, the core 2, the intermediate member 3 which is to be encompassed by the gingiva, and the superstructure 4, in this instance, a jacket crown (facing crown). The epimobile construction of the artificial tooth in this illustrated example is achieved in that the facing or jacket crown 4 is mounted on a sleeve 5 which contains a filling constituted of silicon rubber 6. Approximately centrally of the silicon rubber there is inserted a threaded bolt 7 which, in turn, is threaded into a bore 13 provided with an internal thread in the center of the discshaped intermediate member 3. The intermediate member 3 and the core 2 are here formed of a unitary structure and consist of gold or a gold-plated material; also coming here into consideration is metal ceramic as a material for the manufacture of the intermediate member 3.

Pursuant to the illustrated embodiment of the invention, embedded in the exterior region of a polymer matrix 8 of the tooth root 1 are spherically-shaped particles 9 each being about 1 mm in diameter; for the purposes of clarity, in the schematic illustration according to FIG. 1 such particles are only shown in the upper left hand portion, although the entire periphery of the root 1 is provided in the same manner with a layer formed of spherically-shaped particles 9. The spherically-shaped particles 9 consist of reabsorbable tricalciumphosphate ceramic and, in the illustrated embodiment, are cut away for about one-third of their periphery so that the newly formed bone, upon reabsorption of the material of the spherically-shaped members, can penetrate into the polymer matrix of the root. A thin coating 10 which encompasses the spherically-shaped member is, in contrast therewith, constituted of non- or barely reabsorbable tetracalciumphosphate ceramic.

The gingiva which encompasses the tooth neck, or respectively, the intermediate member 3, is designated by the reference numeral 11 in FIG. 1, while the symbolically indicated jawbone is identified by reference numeral 12.

Figure 2:
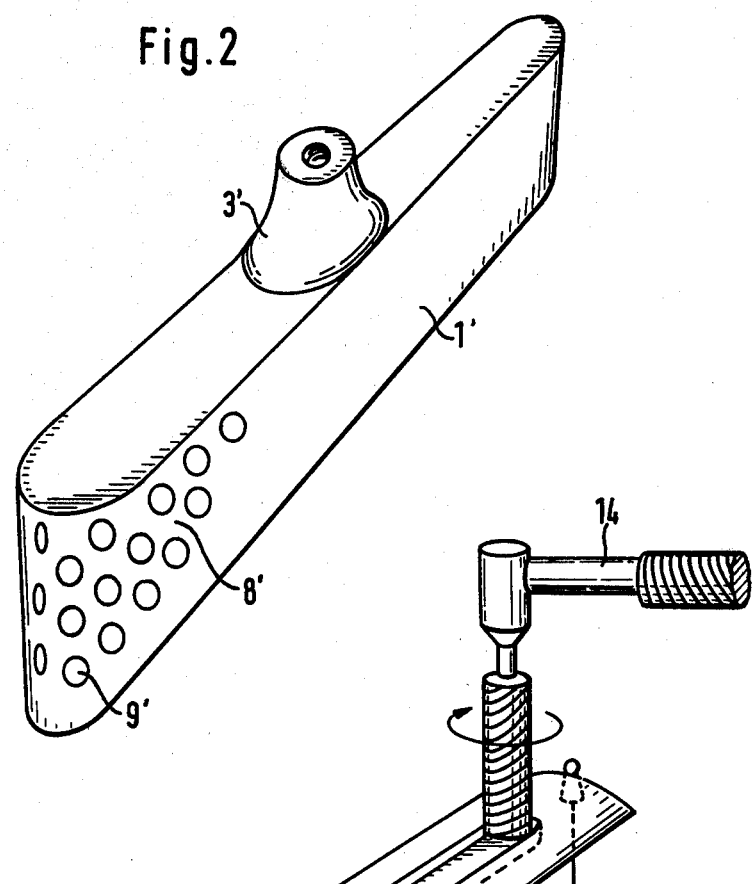
FIG. 2 is a perspective view of another embodiment of the tooth root of the inventive artificial tooth.

The shape of the tooth root 1 of the inventive artificial tooth can be selected almost as desired and correlated with the current anatomical conditions. Whereas in the embodiment according to FIG. 1 the root 1 is in the form of a truncated cone, FIG. 2 illustrates an elongated version 1' of the artificial root which, for instance, is to be preferred as a replacement for a plurality of adjacently positioned teeth, or for the mounting of a highly-loaded fastening element for dental bridges. The tooth neck, in essence, the intermediate member, which should be as completely as possible encompassed by the gingiva is designated in FIG. 2 by reference numeral 3'.

Figure 3:
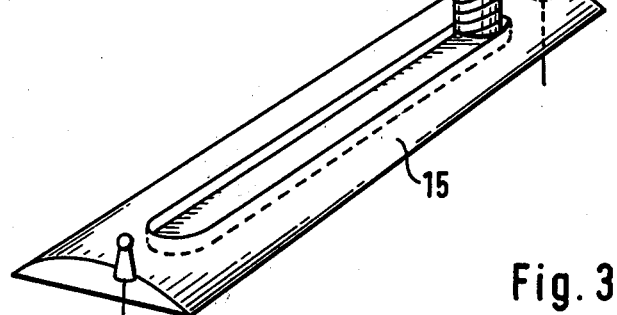
FIG. 3 is a bone milling cutter with an associated template for the manufacture of an implant support for an inventive artificial tooth.

Since the implant support in the jawbone can be worked in most simply with a rotatable cooled bone milling cutter 14 as shown in FIG. 3, the shape of the root 1, 1' is either a rotationally symmetrical cylinder or a truncated cone, or it forms, similar to FIG. 2, an elongated member with semicircularly-shaped ends for which, suitably with the aid of a corresponding milling template 15 (FIG. 3), there can be shaped the implant support in the jawbone.

The curved or concavely conical shape of the intermediate member 3, 3' which is shown in FIGS. 1 and 2 supports the growth of a gingiva which is correlated to natural conditions to this intermediate member, and thereby provides a close or sealed closure of the enossal portion, respectively, the root of the inventive artificial tooth.

In the implanting of the tooth root 1 the inner bore 13 (compare FIG. 1) is suitably closed off through the intermediary of a threaded cap (not shown), which is removed after the growing in of the root 1, 1', whereupon the superstructure 4 may then be inserted with the aid of the threaded bolt 7. A subsequent exchange of the superstructure, in effect, the components 4 through 7, is also possible for such a configuration of the artificial tooth.

The viscoelastic properties of the polymers contained in the sleeve 5 can be varied within wide boundaries and thus optimally correlated with the particular requirements. It is important that the superstructure 4 be so epimobile connected with the root 1 through the sleeve 5 which is filled with the plastic material, that hard shocks caused by misloads, for example, an inadvertent bite on a hard object, can be damped. In addition thereto, this epimobile fastening of the superstructure is adapted to compensate for relative motions which occur upon loadings of the jaw.

What is claimed is:

1. An artificial tooth including an implantable tooth root, said tooth root being essentially constituted of a biostable polymer matrix compatible with human tissue; reabsorbable, bioreactive calciumphosphate in finely dispersed form being introduced in said polymer matrix; a thin, porous layer of essentially non-reabsorbable calciumphosphate encompassing said bioreactive calciumphosphate; a core being inserted in said polymer matrix, said core forming connecting means for mounting of a dental superstructure thereon; and an intermediate member being arranged in the region of the tooth neck encompassed by the gingiva and extending between the tooth root and the dental superstructure, said intermediate member being constituted of a tissue-compatible material supportive of the sealing contact of the gingiva, said dental superstructure being shock-absorbingly connected with said tooth root.

2. An artificial tooth as claimed in claim 1, said dental superstructure comprising a tooth crown.

3. An artificial tooth as claimed in claim 1, said dental superstructure comprising a fastening element for a dental bridge.

4. An artificial tooth as claimed in claim 1, said reabsorbable, bioreactive calciumphosphate being sintered and approximately uniformly embedded in the exterior region of said polymer matrix in the form of substantially spherically-shaped particles each having a diameter of between 0.2 to 1.5 mm, said thin porous layer of non-reabsorbable calciumphosphate being sintered and encompassing said particles.

5. An artificial tooth as claimed in claim 1, said reabsorbable calciumphosphate being tricalciumphosphate and said non-reabsorbable calciumphosphate being tetracalciumphosphate.

6. An artificial tooth as claimed in claim 4, said substantially spherical-shaped calciumphosphate particles being arranged only in the surface region of said tooth root and being cut along about one-fifth to one-half of their peripheral surfaces whereby the essentially non-reabsorbable calciumphosphate in the form of said porous particle layer coating is present only on the side facing towards said polymer matrix.

7. An artificial tooth as claimed in claim 4, comprising a finely dispersed filler material in said polymer matrix, said filler material in comparison to said embedded particles being constituted of sintered, reabsorbable tricalciumphosphate in a quantity of between 10 to 20 percent by weight relative to said polymer matrix.

8. An artificial tooth as claimed in claim 1, said polymer matrix of said tooth root being constituted of tissue-compatible methylmethacrylate, and copolymers, polyethylene, polypropylene, polyphenoloxide.

9. An artificial tooth as claimed in claim 1, said tooth root having a configuration in conformance with the available implantation space.

10. An artificial tooth as claimed in claim 9, said tooth root being rotationally symmetrically constructed.

11. An artificial tooth as claimed in claim 10, said tooth root being cylindrically and reducingly tapered towards the free end thereof.

12. An artificial tooth as claimed in claim 10, said tooth root being conically and reducingly tapered towards the free end thereof.

13. An artificial tooth as claimed in claim 10, said tooth root having an external form and dimension in conformance with the implantation support, said support being formed into the jawbone with the intermediary of a bone milling cutter and associated template.

14. An artificial tooth as claimed in claim 1, comprising a metal sleeve, said dental superstructure being seated on said sleeve; and elastic synthetic material filling said metal sleeve; and a connecting member detachably fastened to the core of said tooth root extending into said elastic synthetic material.

15. An artificial tooth as claimed in claim 14, said elastic synthetic material comprising silicon rubber.

16. An artificial tooth as claimed in claim 14, said connecting member comprising a threaded bolt.

17. An artificial tooth as claimed in claim 14, said intermediate member and the core of said tooth root being a unitary structure of a tissue-compatible metallic material; and an internal bore being formed in said intermediate member for receiving said connecting member and fastening thereto of said dental superstructure.

18. An artificial tooth as claimed in claim 17, said metallic material comprising clad metal.

19. An artificial tooth as claimed in claim 17, said metallic material comprising metal ceramic.

20. An artificial tooth as claimed in claim 1, said intermediate member comprising a disc-shaped member having a concavely curved peripheral edge structure.

* * * * *